United States Patent [19]

Craig

[11] Patent Number: 4,701,239
[45] Date of Patent: Oct. 20, 1987

[54] APPLICATOR FOR APPLYING TWO OR MORE TAPES TO A MOVING WEB

[75] Inventor: Grantland A. Craig, Green Bay, Wis.

[73] Assignee: Paper Converting Machine Company, Green Bay, Wis.

[21] Appl. No.: 787,467

[22] Filed: Oct. 15, 1985

[51] Int. Cl.$^4$ .............................................. B32B 31/18
[52] U.S. Cl. .................................. 156/519; 156/521; 156/552; 226/42; 226/44
[58] Field of Search ............... 156/511, 519, 552, 521; 226/42, 44

[56] References Cited

U.S. PATENT DOCUMENTS

| | | |
|---|---|---|
| 2,990,081 | 6/1961 | De Neui et al. |
| 3,728,191 | 4/1973 | Wierzba et al. |
| 3,960,646 | 6/1976 | Wiedamann |
| 4,001,072 | 1/1977 | De Neui |
| 4,267,004 | 5/1981 | Anderson ............... 156/361 |
| 4,341,580 | 7/1982 | Amhed .................. 156/195 |
| 4,561,581 | 12/1985 | Kelly ...................... 226/42 |

Primary Examiner—Donald E. Czaja
Assistant Examiner—Merrell C. Cashion, Jr.
Attorney, Agent, or Firm—Tilton, Fallon, Lungmus & Chestnut

[57] ABSTRACT

A tape applying apparatus to advance, cutoff, and transport two or more adhesive covered tape strips and apply same to a continuously moving series of connected diapers before the diapers are cut into discreet products; the apparatus being arranged so that the distance between two consecutive tapes is different from the distance between two other tapes, and all tapes so applied will be cut at equal lengths; and since different spacing requires different tape feed speeds, the invention includes two tension isolating and feed roll pairs arranged to allow an excess of tape to be looped therebetween, including loop detection devices which rotate the first and second tension isolating roll pairs at different speeds to maintain said loop of excess material within predetermined minimum and maximum limits.

5 Claims, 5 Drawing Figures

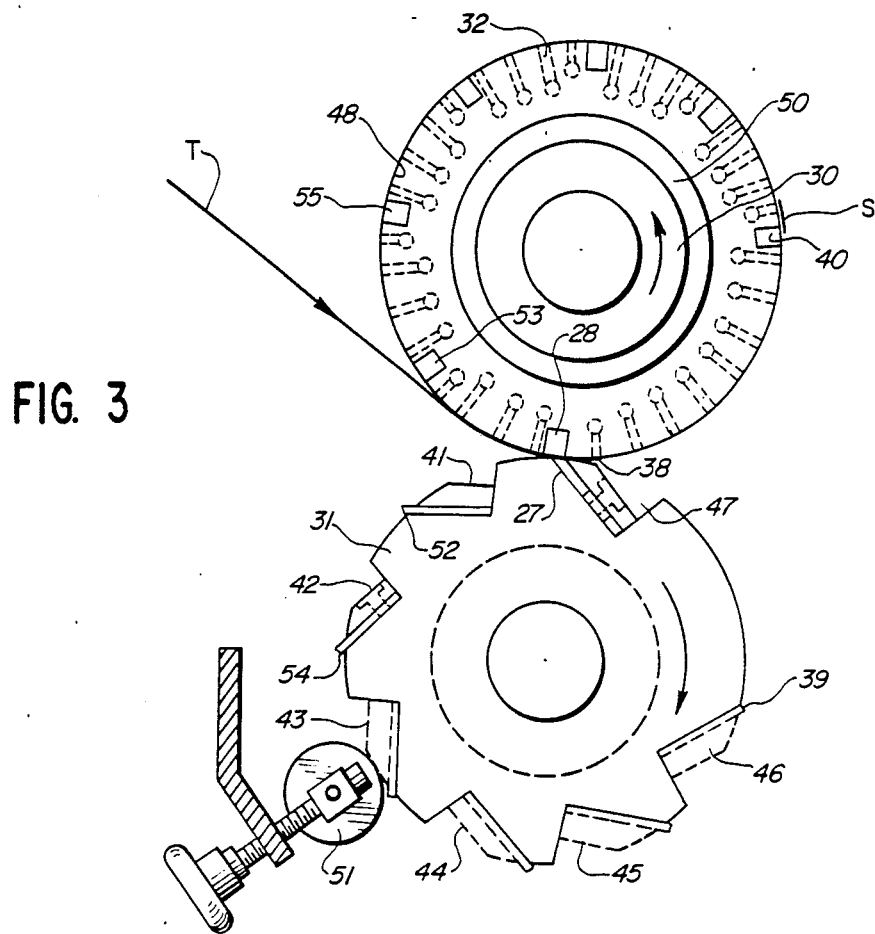
FIG. 3
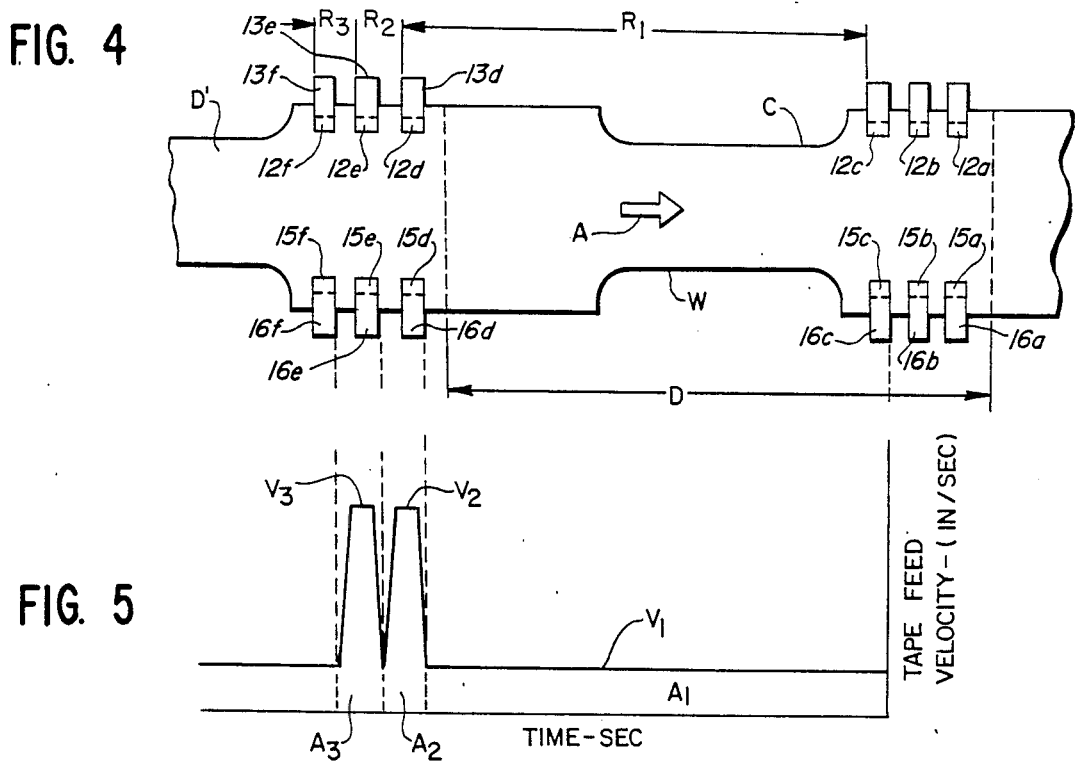
FIG. 4
FIG. 5

APPLICATOR FOR APPLYING TWO OR MORE TAPES TO A MOVING WEB

BACKGROUND AND SUMMARY OF INVENTION:

This invention relates to an applicator for applying two or more tapes to a moving web and, more particularly, to tape tabs which are used on diapers and incontinent pads.

Disposable articles such as incontinent pads, surgical dressings, baby diapers, and the like, are frequently held in place during use by tape tabs which are attached after the product is fitted snugly to the user's body. Illustrative is U.S. Pat. No. 2,990,081 which describes a device for intermittently withdrawing a length of tape from a supply roll, wrapping this around an arcuate portion of a backing roll, cutting segments therefrom, and advancing the cut segment such that it is applied to the product at the same speed as product movement. Patent '081 shows the basic theory used in all of the prior art devices whereby a portion of the outside surface of an anvil roll is in close proximity to a web substrate passing between the anvil roll and a backup roll.

Normally the non-sticky portion of the tape is entrained around this moving surface, and slips thereon (because it is still connected to the supply roll) until a cutoff knife roll coacts with the anvil to sever that portion which has advanced beyond the point at which cutoff occurs. Between the supply roll and entrainment around the anvil roll, the tape (usually with a removable release strip adhered to the sticky surface) passes through the nip of a feed roll pair which advances the tape and release strip at a speed substantially less than the speed of the product to which it will be attached. In effect, each of the prior art devices feeds combined strips of tape and release at a substantially uniform rate of feed, and after minor portions of the tape have been cut by coaction of the anvil and cutoff roll, they are held against the surface of the anvil roll by vacuum and are subsequently transported and transferred to the substrate medium such as a diaper, incontinent pad, etc.

These known devices essentially feed tape and release strip on the basis of one per machine revolution. It is also known that prior art devices apply individual tape tabs with release strips at equally spaced intervals onto the moving web or product. These devices have been frequently used and are quite acceptable even at high speeds when applying single tape tabs to articles such as disposable diapers. Also, in practice, two side-by-side tape applying means are used such that each side of the diaper receives one tape.

In the past few years, a number of product improvements have made disposable diapers and pads much more comfortable as well as more functional, and these improvements have generally allowed upsizing of disposable diapers so they can be used for adults.

By using two of the tape applying devices described above and further in U.S. Pat. Nos. 3,728,191, 3,960,646 and 4,001,072, two or more tapes with release strips can be applied to each incontinent pad or adult diapers, and by phasing each of the units differently, tape width (measured in the MD) and the distance between tapes can be altered to suit. However, the known units cannot apply two or more tapes to a single pad or diaper, nor do they have the ability to apply two tapes with spacing different from two other tapes in a series.

This invention is directed toward tape applicators that can apply two or more tapes per diaper to a continuously moving web of connected diapers such that spacing between consecutive pairs is different. In the particular embodiment disclosed, the invention includes an anvil roll constructed with a plurality of anvils and blades such that three tape tabs with release backing can be placed on each side of three different sizes of pads. In effect, a single device is capable of attaching three tapes to each side of a diaper being processed, and by changing over the position of cutoff blades and anvils, the same device can be used to place three tape tabs (with different spacing between tapes) on a second size pad. Still a third set of three tapes with a still different spacing therebetween can be placed on a third size of pad by making adjustments to the same device.

FIG. 3 is a fragmentary, enlarged side elevation view of the tape, cutoff and advancing roll set, as along line 3—3 of FIG. 2;

FIG. 4 is a plan view of an incontinent pad or disposable diaper showing typical placement of multiple tapes; and FIG. 5 is a graph showing tape velocity as a function of time during one pad feed cycle.

Figure 1:
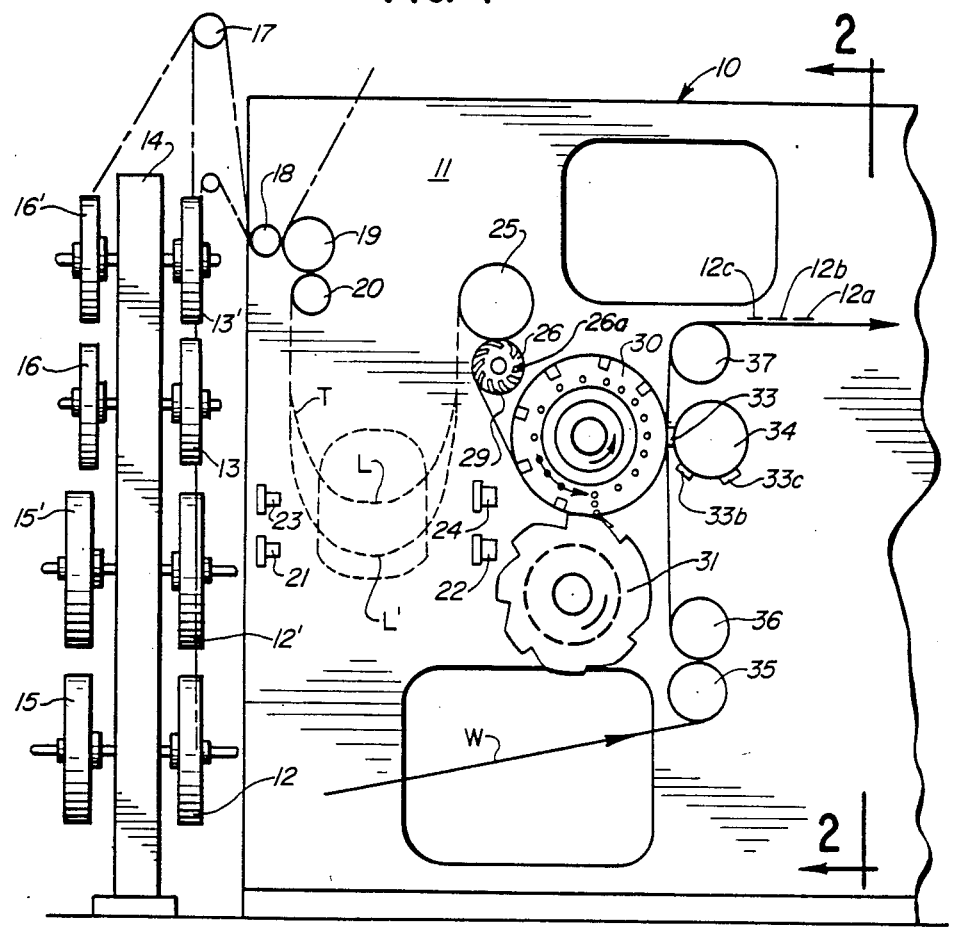
FIG. 1 is a side elevation of a tape applying system including a multi-spindle unwind stand shown at the left.

DETAILED DESCRIPTION:

The tape advancing, cutoff and transport system 10 of this invention is shown in FIG. 1 with major components thereof mounted in side frames 11 (see FIG. 2) extended to support other components of a diaper assembly machine. In the left hand portion of FIG. 1, supply rolls or reels 12 of adhesive-covered tape and release strip 13 are supported by stand 14 and are joined in superposed fashion prior to entry into the tape cutoff-transport system. Duplicate rolls 12' and 13' are standby rolls which provide the tape and release strip supply after the rolls 12 and 13 have been exhausted. Stand 14 also supports similar rolls 15 and 16 as well as standby rolls 15' and 16', which are joined and placed on the opposite side of the product (also see FIG. 4).

While stand 14 in FIG. 1 is shown feeding web stock at right angles to the machine, it will be recognized that the supply rolls can be arranged so that the web plays out in the direction of product flow (to the right in FIG. 1). From the supply roll positions shown on stand 14, the tape or release strip webs can be longitudinally folded or twisted 90°, if desired, and subsequently pass over guide rollers 17 and lay-on roll 18 before entering the nip of a first pair of draw rolls 19, 20—one of which is driven at a predetermined speed by a separate moter drive (not shown).

Figure 2:
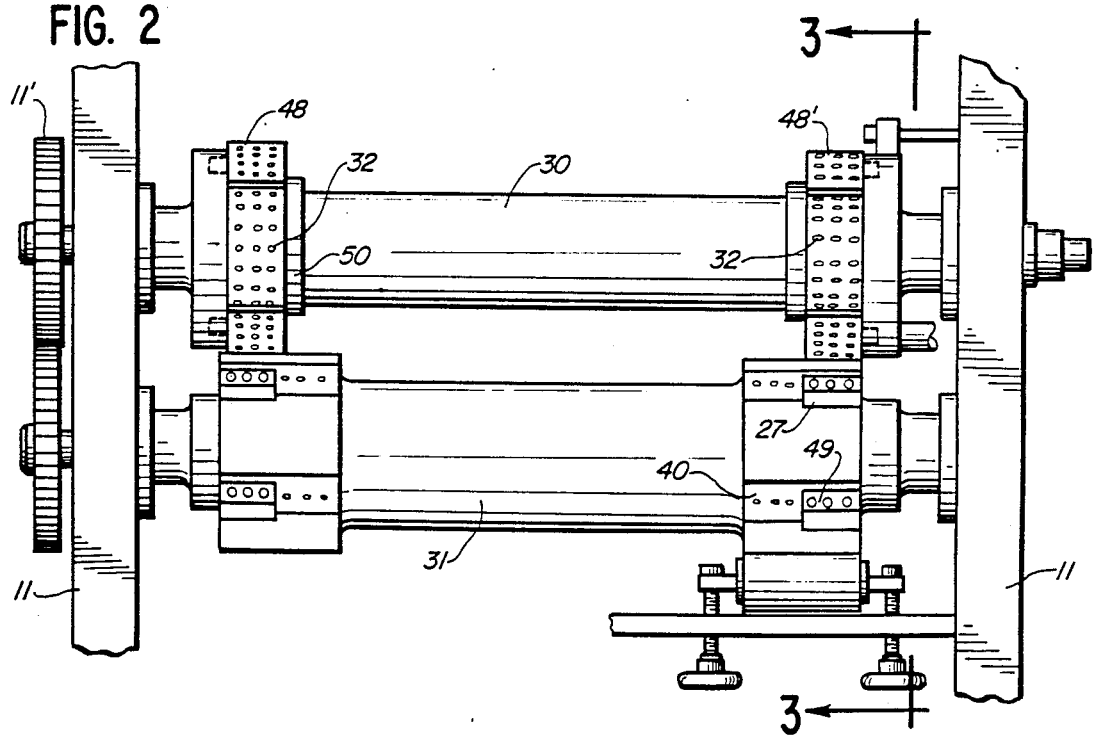
FIG. 2 is a front elevation view of the tape, cutoff and advancing rolls, taken along line 2—2 of FIG. 1.

The drive, however, is a servo motor manufactured by International Cybernetics Corp., designation Type CLU-16R, Model P-1320. It is coupled to the draw rolls 19, 20 by conventional gears such as is shown in FIG. 2 at 11' for other rolls.

The servo drive motor, which rotates draw rolls 19, 20, is controlled by signals from web sensing devices such as a photoelectric eye sensor 21 and receiver 22, which detects the maximum loop L' of combined tape and release strip formed as the pre-combined tape and release strip is fed from roll pair 19, 20 into a tensionless loop. A second sensing device, including photoelectric sensor 23 and receiver 24, also detects the minimum position L of tensionless web. These two signals are fed as inputs to a microprocessor (also not shown) which causes the servo drive motor for roll pair 19, 20 to be actuated and controlled so that the combined tape and release strip is controlled between upper limit L and lower limit L'. In the preferred embodiment, the tape web loop is shown tensionless. However, a pivoting dancer roll can bear against the web and thereby induce low levels of web tension. A suitable microprocessor for the inventive apparatus is designed Model 3220 and manufactured by International Cybernetics Corp.

The digital signal that controls speed of the drive motor for roll set 19, 20 also takes into account rotation of draw rolls 25 and 26, which in turn draw material from the tensionless loop and tend to decrease the loop from position L' to the upper limit L.

As will be described hereinafter, the velocity of roll pair 25, 26 is varied from time to time during a diaper cycle, each velocity being held for a predetermined period—see generally FIG. 5. The predetermined time period is a function of spacing between tape tabs and the different tape feed velocities are functions of the time period available. Since tapes of equal length (minor dimension in FIG. 4) are used at three locations, the time available for tape feed is determined by the peripheral spacing between consecutive cutoff or tape severing means, but in effect, equal tape lengths are advanced for cutoff and subsequent transfer by maintaining a relatively low velocity over an extended period of time, and for subsequent tapes on the same diaper, feeding additional tape at relatively high velocities for a very short period of time.

Rubber nip roll 26 of FIG. 1 has grooves 26a arranged in substantially radial fashion—similar to vanes on a fan. At the instant of tape tab cutoff, tape is pinched between the tip of the blade 27 and anvil 28 (see central portion of FIG. 3) both of which travel at substantially the same speed as the web W. Because tape velocity, as dictated by the speed of draw roll pair 25 and 26, is less than the speed of the advancing web W, this speed mismatch would cause tearing of fibres and ragged tape cutoff. By allowing resilient segments 29 defined by grooves 26a to deflect when high tape web tension is present (for example, at cutoff), the tape web T advances at the same speed as web W during the instant of cutoff, and a clean cut edge results from the grooved arrangement of rubber roll 26.

The path of travel or advancement of the release strip-covered tape T, after leaving draw roll 26 encounters the vacuumized transfer roll 30 which, like the other rolls, is rotatably mounted in the frames 11. In the illustration given, the vacuumized transfer roll 30 is equipped with anvils while the rotatably mounted cutoff roll 31 is equipped with knives. The knives cooperate with the anvils in transversely severing the tape T.

At the same time that the tape is being advanced for cutoff between the co-acting anvil-equipped transfer roll 30 and knife-equipped cutoff roll 31, a moisture-impervious web W passes the surface of the transfer roll 30 in touching contact with the surface. The peripheral speed of transfer roll 30 is the same as web W and before cut off the tape slips on the faster moving anvil roll 30. When a discrete length or segment of continuous web T is severed between the anvil and knife rolls 30, 31, transversely arranged vacuum holes 32 (see FIG. 2) in the surface of vacuumized transfer roll 30 hold the cut segment firmly against the roll surface, thus allowing for high speed transport on the surface of the anvil roll and transfer-adhesion to web W as it is pressed between the surface of roll 30 and raised pressure pads 33, 33b and 33c of backup roll 34.

Web W is fed to the machine through nip draw roll pair 35, 36 which are driven at the same surface speed as the continous ribbon of connected diapers. A first series of tapes 12a, 12b and 12c are attached to web W (see also FIG. 4) and are transported downstream over guide roll 39, whence they are joined and adhesively secured to other components of the diaper assembly—including the absorbent fluff core, top cover sheet of fluid pervious nonwoven, etc. After all elements of the diaper are assembled into a complete ribbon or continous web of components, the continous web is severed to produce individual diapers, which are then folded and delivered in pre-counted stacks for subsequent cartoning.

Thus, web W follows a first path between the side frames 11, which leads to the nip between the transfer roll 30 and the backup roll 34. Adhesive is placed advantageously on the tape prior to reeling. As the tape is unreeled and conducted through a second path including the loop L, L', the rolls that the adhesive coated side passes over are silicone release coated.

In the preferred embodiment of the invention as shown in FIGS. 1-3, multiple cutouts and mounting arrangements are provided in the knife roll 31 and multiple anvils mounted in the vacuumized anvil roll 30. While the knife and anvil rolls of the preferred embodiment are arranged to cut off a series of three consecutive tape tabs for each of the three different diaper sizes, depending on knife location and placement, the invention advantageously provides for the cutoff, transfer, and application of two or more tapes to a continuously moving web. In practice, it is desireable to have several sizes of commercial product, that is, pads of different lengths and widths. Generally, length and width increase or decrease together.

In FIG. 3, the leading edge 38 of the combined adhesive and release strip is shown to the right of the tip of blade 27. This represents the tape position and operation of the cutoff rolls 30, 31 at the instant of tape segment cutoff. As shown in FIG. 3, a portion of continuous tape web T is in contacting relationship with the surface of roll 30 and held thereon by vacuum being drawn through ports 32. On further rotation of the rolls 30, 31, a segment S of tape is cut off and held by the row of vacuum ports (see FIG. 2) directly ahead of each anvil.

Tape segment S shown at the 3 o'clock position on the upper roll of FIG. 3 is the segment cut by a blade mounted in position 54 of the lower roll 31 and co-acting anvil 40 of the vacuumized anvil roll 30.

In the preferred embodiment, cutouts 41 through 47 provide different mounting positions for the blades—the choice of positions depending on the predetermined distance between tapes. In the preferred embodiment, the distance between cutouts 42 and 47 is equal to the distance between the last tape of one diaper and the first tape in the next diaper of a series. The distance between cutouts 47 and 41 will also be the same as the distance between cutoff of the first and second tapes on each diaper. The distance beteeen cutouts 41 and 42 will be the same as the distance between second and third tapes on each diaper. Cutout 43 is used as a common mounting position for the last tape of the first diaper size and the first tape of the second diaper size—thus seven cutouts in roll 31 provide for nine different tape locations—three tapes on each of three different diaper sizes.

FIG. 2 shows that the vacuumized anvil/transfer roll section 48 is relatively narrow, for example, 3" to 4". In FIG. 2, roll segments 48 and 48' are shown adjusted for a wide product, hence, blades such as 27 held by holders 49 are mounted in the outside position of the various cutouts 41-47. The central portion of roll 28 is reduced in diameter to minimize machining; however, the cutouts 41-47 could be machined in a full width roll face if necessary. For narrower products, blade holders 49 are removed, blades 29 moved toward each other, and the anvil roll segment 48 and mounting sleeve 50 are slidably moved toward the central portion of roll body 30.

A drip oiler or oil injection can be used to saturate the surface of roll 51 with lubricant, and the oil impregnated soft surface of roll 51 lubricates each blade as it rotates past the stationary lubricator, which is adjustable relative to the axis of rotation of the blade roll 31.

FIG. 4 shows a diaper D and part of the following diaper D' as portions of a continous web W of materials moving in direction of the central arrow A. The diaper D is narrowed in crotch section C and is usually provided in several lengths and widths.

While FIG. 2 shows that two sets of blade positions and two sets of anvil segments are needed for applying tape to both sides of the pad, the following description is in terms of one side of the diaper and tape location. In FIG. 3, cutout 47 will cut off the first tape segment, which is shown with its leading edge at position 38 extending beyond the point of cutoff. Since the tape 12 and release strip 13 are combined prior to cutoff and application to the diaper web W, reference to advancing, cutoff, or transport of tape segments necessarily means both the tape itself and the attached release strip.

In FIG. 3, the tape segment being cut by blade tip 27 is typical of tape 12a shown in FIG. 4. The tape segment cut by co-action of blade 52 and anvil 53 corresponds to 12b of FIG. 4, and the tape segment cut by blade 54 and coacting anvil 55 corresponds to tape 12c. The corresponding tapes on a subsequent diaper in a series are 12d, 12e and 12f. In FIG. 3, blades and blade holders mounted in cutouts 43 through 46 are shown in phantom since they would not normally be installed except for a different size diaper and different spacing between tapes. For example, blades would be mounted in the cutouts 47, 41 and 42 to position the tapes properly on one size of diaper, cutouts 42, 43 and 44 for a second size and in cutouts 44, 45 and 46 for a third size. Thereafter, the tapes are applied sequentially by pads 33, 33b and 33c relative to tapes 12a, 12b and 12c, for example.

The release tapes 13d, 13e, and 13f have a transverse dimension which is less than the transverse dimension of the corresponding adhesive tapes 12d, 12e, and 12f (see also FIG. 1). A portion of the adhesive coating is therefore exposed for securing the adhesive tape to the diapers. The adhesive tapes and corresponding release tapes on the other side of the diapers are designated 15a-f and 16a-f.

In FIG. 3, the peripheral distance (measured counterclockwise) between blade 54 and blade 27 is equal to the repeat distance $R_1$ between cutoff of the last tape on a first diaper and cutoff of the first tape on the next diaper. The peripheral distance between blade 27 and the blade 52 represents the repeat distance from the rear edge of tape 12d to the rear edge of tape 12e— see $R_2$ in FIG. 4. Peripheral distance between blades 52 and 54 as well as anvils 53 and 55 is the repeat distance $R_3$ from the cut edge of tape 12e to the cut edge of tape 12f. In effect, the peripheral spacing between blades determines spacing between adjacent tapes as they are attached on a given pad.

FIG. 5 represents a tape feed velocity diagram. Since the spacing between different tapes is not equal, and since all tapes on a pad must have equal width, FIG. 5 illustrates that different feed velocities are required to compensate for the unequal spacing. For example, the area $A_1$ under the velocity segment $V_1$ equals the area $A_2$ and $A_3$. However, it is noted that velocities $V_2$ and $V_3$ are equal to each other but much higher than $V_1$.

To illustrate a typical application, certain values are assigned to the tape tab location, etc., in terms of FIG. 4. With a diaper length D of 30" and a speed of 200 diaper pads per minute, the speed of web W equals 6,000 inches per minute. Each second, 100 inches of web material W will pass a fixed point.

At 100 inches per second, the diaper web W travels a distance R in 0.225 seconds and, therefore, in this time period, the tape feed nip rolls 25, 26 advance a tape $1\frac{1}{4}$" long. The speed of tape advance $V_1$ averages 5.55 inches per second. Typical spacing between tape 12d and tape 12e is 3.75 inches and, therefore, for a proper length of tape to be fed for placement as tape 12d and 12e, the tape velocity $V_2$ must be equal to 33.3 inches per second. Likewise, tape feed velocity $V_3$ for the last tape will also be equal to $V_2$ at 33.3 inches per second.

The input and output signals for the various feed roll pairs and the stepping motor drive system for the tape advance as described above thus provides for the variable speed tape advance needed for the inventive system.

While in the foregoing specification a detailed description of an embodiment of the invention has been set down for purpose of illustration, many variations in the details hereingiven may be made by those skilled in the art without departing from the spirit and scope of the invention.

I claim:

1. A tape advancing, cutoff, and transport apparatus for a disposable diaper or the like comprising:
   a frame,
   first supply roll means operatively associated with said frame for supplying an adhesively coated continuous tape,
   second supply roll means operatively associated with said frame for supplying a continuous release tape,
   guide means on said frame to direct said adhesive and release tapes in superposed relation through a nip to feed and adhesively join said tapes, the width of the release tape being less than the width of the adhesive tape whereby a portion of the adhesive is exposed.
   a vacummized transfer roll with anvils mounted thereon,
   a co-acting knife cutoff roll having a plurality of cutoff knives mounted at different locations around the periphery of said cutoff roll to cut segments of said joined adhesive and release tapes, and
   a backup roll which supports a continuous web between the transfer roll and the backup roll while the exposed adhesive portion of said segments is adhered to the web.

2. The apparatus of claim 1 wherein the spacing between one pair of consecutive cutoff knives is different from the spacing between a different pair of consecutive cutoff knives.

3. The apparatus of claim 1 including a pair of draw rolls for feeding the adhesively joined adhesive and release tapes to the transfer roll, one of the draw rolls having a resilient surface with transverse grooves arranged in a substantially radial orientation to form resilient roll segments whereby tension on said adhesively joined tapes wrapping a portion of said one roll surface will cause deflection of the roll segments between adjacent grooves to reduce tension in the tapes during cutoff.

4. The apparatus of claim 1 wherein concentrically machined segments of said knife or said anvil roll are slidably adapted to apply tape segments to different web widths.

5. The apparatus of claim 1 in which said cutoff roll and said transfer roll have a plurality of knife and anvil mounting locations whereby the peripheral spacing between adjacent knives and adjacent anvils can be adjusted.

* * * * *